United States Patent [19]

Moore

[11] Patent Number: 4,524,602

[45] Date of Patent: Jun. 25, 1985

[54] ACCIDENT RECONSTRUCTION DEVICE

[76] Inventor: Milton D. Moore, 2268 Park Cir., Baton Rouge, La. 70819

[21] Appl. No.: 587,052

[22] Filed: Mar. 7, 1984

[51] Int. Cl.³ .............................................. G01N 19/02
[52] U.S. Cl. ............................................. 73/9; 73/146
[58] Field of Search ............................. 73/9, 8, 146, 7

[56] References Cited

U.S. PATENT DOCUMENTS

| 886,691 | 5/1908 | Fowler | 73/146 |
| 1,415,287 | 5/1922 | Wooster | 73/146 |
| 4,187,714 | 2/1980 | Cox et al. | 73/9 |

FOREIGN PATENT DOCUMENTS 56-140210  11/1981  Japan ........................................ 73/9

Primary Examiner—Kenneth M. Schor
Attorney, Agent, or Firm—William David Kiesel

[57] ABSTRACT

An accident reconstruction device is provided which allows for simple and accurate measurement of the coefficient of friction for a given surface. The device comprises a metal H-beam, I-shaped in vertical section, having a rubber tire tread affixed to its lower flange and a hole at one end positioned at the vertical center of mass of the device. The device is pulled along the surface to be tested by a scale which indicates the force required to move the device, thus allowing calculation of coefficient of friction for the surface. By turning the device over, the coefficient of friction between metal and the surface can also be determined by the same device, thus rendering the device particularly useful in determining a composite coefficient of friction for automobile accidents where an automobile has skidded over different surfaces, both on its tires and on metal portions of the automobile body.

6 Claims, 2 Drawing Figures

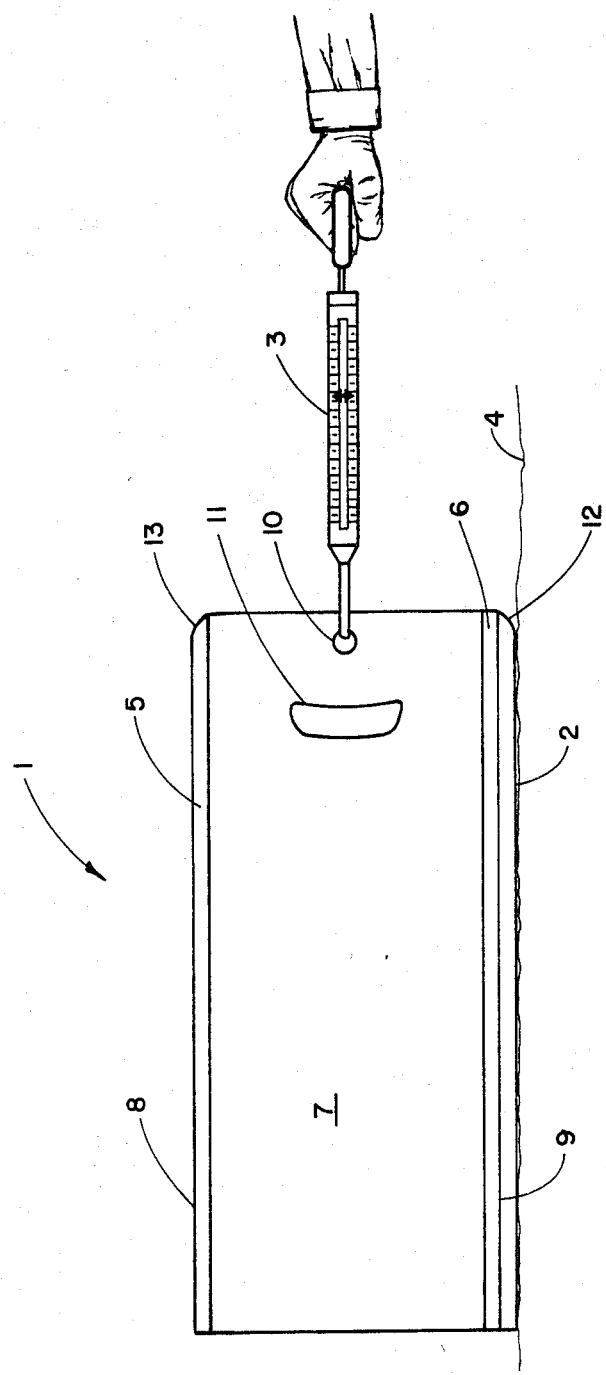
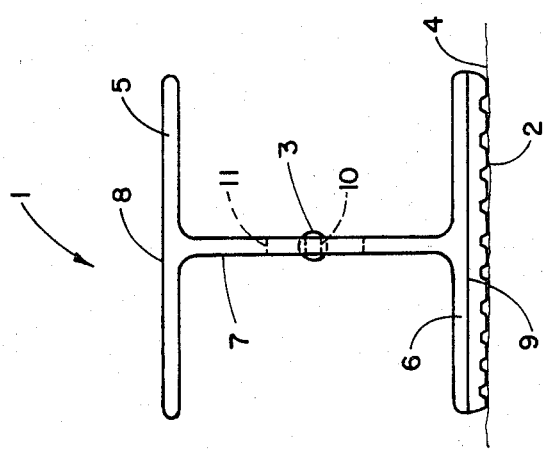
FIGURE 2
FIGURE 1

ACCIDENT RECONSTRUCTION DEVICE

BACKGROUND OF THE INVENTION

This invention relates generally to devices which determine the coefficient of friction between two surfaces, and, more particularly, to devices which may be used to determine the coefficient of friction between surfaces involved in automobile accidents.

In order to determine the speed at which an automobile was traveling at the time of its brakes locking, a police officer or investigator must determine the coefficient of friction between the vehicle and the surface or surfaces over which the vehicle skidded. A simple formula is used to calculate this data. For a single surface, the formula is $f = s^2/30(d)$ where $f$ = coefficient of friction, $s$ = speed of vehicle in miles per hour, and $d$ = distance of skid in feet. A value for the coefficient of friction $f$ between two given surfaces can be calculated by the amount of force required to move one surface at a steady rate across the other. If W represents the weight of the moving body and P represents the force required to move the body, $f = P/W$. Where the type of surface changes over the length of the skid (either the vehicle or the roadway surface), a composite formula must be utilized: $s^2 = 30(f_1 d_1 + f_2 d_2 + f_3 d_3 \ldots)$, where the subscripts indicate the varying values of f and d for each different combination of surfaces. The type of roadway surface can vary over the length of the skid (e.g. asphalt, concrete, gravel, soil, grass, etc.). Just as the roadway surface may vary, so may the vehicle surface (e.g. tires or some metal surface of the vehicle).

An accident investigator, in order to accurately determine the variables in the above formulae, should take measurements at the scene of the accident under the same conditions as those of the accident. One method which has been employed is accomplished by the investigator skidding his own vehicle over the surface, taking measurements to determine the coefficient of friction for the surface and then applying the coefficient to the data from the accident. This method is often inaccurate and in many cases impossible because of safety considerations.

As result of these problems, devices have been designed for determining the coefficient of friction at the scene of an accident. Examples of such devices may be found in the following patents:

| U.S. Pat. No. | Inventor | Title | Issue Date |
|---|---|---|---|
| 3,301,039 | Kummer | Skid Resistance Drag Tractor | 1/31/67 |
| 3,538,742 | Benning | Friction Measurement | 11/10/70 |
| 4,130,008 | Broshears | Device for Measuring Friction & Distance | 12/19/78 |
| 4,144,748 | Vinogradov, et al | Device for Determining Coefficient of Adhesion of Pneumatic Wheel Tires of Transport Vehicles to Road Pavement | 3/20/79 |
| 4,187,714 | Cox, et al | Surface Friction | 2/12/80 |
| 4,315,426 | Brandon | Friction Coefficient Measurement from a Moving Vehicle | 2/16/82 |

Some of these devices are trailer-mounted (e.g. U.S. Pat. Nos. 3,538,742 and 4,144,78) and as such are difficult to use off standard roadway surfaces. These devices are also usually too great in size to be carried in a police car. Other devices, such as U.S. Pat. No. 4,315,426, must be added to a vehicle, resulting in unnecessary expense as well as being difficult or impossible to operate off the roadway. Also, because the trailered and add-on devices have linkage arrangements for force measurement, accuracy may be lost.

More simplistic devices have been designed which may be carried in the vehicle of an officer investigating at the accident scene. Examples of these devices are the Broshears patent (U.S. Pat. No. 4,130,008) and the Cox patent (U.S. Pat. No. 4,187,714). These devices have proven inaccurate due to the "gearing effect", or rotational force, which results when the device is pulled at a point above the center of mass of the device. In order to permit consistent and accurate readings, the pulling force should be applied at the center of mass of the device in a direction parallel to the road surface or other surface to be tested. The accuracy of the Cox device is further impaired by the squared edge of the friction surface (usually a tire tread) which will tend to dig into the roadway when the rotational force is applied. In order to counteract the rotational force, the devices can be pulled at an angle other than parallel to the roadway. However, inaccurate and inconsistent readings will also result from such an application of force.

Compounding the above problems is the fact that, in order to apply the prior art devices in situations where something other than a tire has skidded (such as a vehicle on its side), the friction surface on the device must be changed.

The need therefore exits for a friction measuring device which is compact, easy to use, distributes weight evenly, and yields consistently accurate results.

SUMMARY OF THE INVENTION

Considering the above, it is an object of this invention to provide an accident reconstruction device which is compact, inexpensive and which measures the coefficient of friction between two surfaces with consistently accurate results.

It is another object of this invention to provide such a device which can quickly and easily determine the coefficient of friction between a tire tread and another surface as well as between metal and another surface.

Still further objects and advantages of this invention shall become apparent from the ensuing descriptions of the invention.

Accordingly, an accident reconstruction device is provided comprising an elongated metal body, I-shaped in section, having upper and lower flanges connected by a web and having a hole through the web at the vertical center of mass of the body; a test surface affixed to the lower flange; and a scale means, attachable to the hole, for pulling the body and indicating the force required to pull the body.

BRIEF DESCRIPTION OF THE DRAWINGS

FIG. 1 is an end view of a preferred embodiment of the invention.

FIG. 2 is a side view of a preferred embodiment of the invention.

DESCRIPTION OF PREFERRED EMBODIMENTS OF THE INVENTION

As shown in FIG. 1, the invention generally comprises a body 1, friction surface 2 and a scale means 3. The body 1 rests upon the traveled surface 4, usually a roadway. As the body 1 is pulled along the traveled surface 4 at a steady rate by the scale means 3, the force required to do so is indicated on the scale means 3, enabling one to determine the value of the coefficient of friction between the two surfaces using the above described formula, $f=P/W$. In order to obtain accurate readings, the body 1 must be pulled along its vertical center of mass and parallel to traveled surface 4. Because of this requirement, it is preferred that the overall height of body 1 be approximately eight inches.

As shown in FIGS. 1 and 2, the body 1 is an I-shaped member, ideally a section of steel beam, having an upper flange 5 and a lower flange 6 connected by a web 7. The upper and lower flanges, 5 and 6, have flat upper and lower surfaces, 8 and 9 respectively. The body 1 is provided with a hole 10 through the web 7 near one end. The hole 10 must be located at the vertical center of mass of the body. In a preferred embodiment, an opening 11 is provided through the web 7 to facilitate handling. The unique shape of the body 1 allows for even weight distribution, resulting in extremely accurate measurements.

The friction surface 2, usually a rubber tire tread, is affixed to lower surface 9. In a preferred embodiment the friction surface 2 is rounded on its leading edge 12. The upper flange 5 is also rounded on its leading edge 13. This construction allows for more accurate readings by preventing the leading edges 12 and 13 of the device from snagging the traveled surface 4.

The scale means 3 is provided for pulling the body 1 and indicating the force required to pull the body 1 across the traveled surface 4 at a steady rate. The scale means must be attachable to the hole 10 in order to pull the body 1 at its vertical center of mass. The scale means 3 is usually a calibrated spring scale capable of indicating the force required to pull the body 1.

Thus, in order to determine the coefficient of friction for a vehicle tire across a specific traveled surface 4, the invention is placed upon the traveled surface 4 with the friction surface 2 (here, a rubber tire tread) bearing against the traveled surface 4. The body 1 is then pulled in a direction parallel to the traveled surface 4 using the scale means 3. The amount of of force required to pull the body 1 at a steady rate after static friction is overcome is then divided by the total weight of the body 1 and friction surface 2 in order to determine the coefficient of friction. A separate value is determined for every surface over which the tire has skidded. In order to determine a coefficient for metal skidding over the same surface, the device is simply turned over such that the upper surface 8 is bearing against the traveled surface 4, and the process is repeated. The skid marks are then measured and the aforementioned formulae are employed to calculate the speed. The preferred use of a steel beam section of the body 1 allows for excellent measurement results. Using the preferred eight inch height, a section of steel beam can be chosen weighing from 35 to 50 pounds, which is easily transportable and which yields accurate results.

Thus, as can be seen, an accident reconstruction device is provided which may be used to simply and accurately determine the coefficient of friction between two surfaces. The same device may be used, without modification, to detemine the coefficient of friction between a vehicle tire and a road surface, as well as between a metal part of the vehicle and the same road surface. The device is easily transportable and inexpensive to make. There are, of course, many alternate embodiments not specifically described but which are intended to be included within the scope of this invention as defined by the following claims.

I claim:

1. An accident reconstruction device, comprising:
    (a) an elongated metal body, I-shaped in section, having upper and lower flanges with corresponding flat upper and lower surfaces, said flanges being connected by a web having a hole through said web at one end, said hole positioned at the vertical center of mass of said body;
    (b) a flat friction surface affixed to and substantially covering said lower surface of said lower flange; and
    (c) a scale means, attachable to said hole, for pulling said body and indicating the force required to pull said body.

2. An accident reconstruction device as described in claim 1, wherein the edges of said friction surface and said upper flange on the same end as said hole are rounded.

3. An accident reconstruction device as described in claim 2, wherein said body is a portion of a steel beam.

4. An accident reconstruction device as described in claim 3, wherein said test surface is a rubber tire tread.

5. An accident reconstruction device as described in claim 4, wherein the height of said body is approximately eight inches.

6. An accident reconstruction device as described in claim 5, wherein said body further comprises an opening through said web, for carrying said body.

* * * * *